US010076404B2

(12) United States Patent
Bonnette

(10) Patent No.: US 10,076,404 B2
(45) Date of Patent: Sep. 18, 2018

(54) CATHETER SYSTEM WITH BALLOON-OPERATED FILTER SHEATH AND FLUID FLOW MAINTENANCE

(71) Applicant: Medrad, Inc., Indianola, PA (US)

(72) Inventor: Michael J. Bonnette, Minneapolis, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 605 days.

(21) Appl. No.: 13/795,248

(22) Filed: Mar. 12, 2013

(65) Prior Publication Data
US 2014/0277075 A1    Sep. 18, 2014

(51) Int. Cl.
A61M 29/00 (2006.01)
A61F 2/01 (2006.01)
A61M 25/10 (2013.01)

(52) U.S. Cl.
CPC .......... *A61F 2/013* (2013.01); *A61M 25/1002* (2013.01); *A61F 2230/0058* (2013.01); *A61F 2230/0071* (2013.01); *A61F 2230/0091* (2013.01); *A61F 2250/0003* (2013.01); *A61M 2025/1081* (2013.01)

(58) Field of Classification Search
CPC .............. A61F 2230/0006; A61F 2/013; A61F 2250/0003; A61F 2/01; A61M 25/104
USPC ...... 604/194, 198, 200; 606/96.01; 623/1.11
See application file for complete search history.

(56) References Cited

U.S. PATENT DOCUMENTS

| 5,954,745 A | 9/1999 | Gertler et al. |
| 6,340,364 B2 | 1/2002 | Kanesaka |
| 6,485,500 B1 | 11/2002 | Kokish et al. |
| 6,511,503 B1 * | 1/2003 | Burkett ................... A61F 2/013 606/200 |
| 6,676,637 B1 | 1/2004 | Bonnette et al. |
| 6,994,718 B2 * | 2/2006 | Groothuis et al. ............ 606/200 |

(Continued)

FOREIGN PATENT DOCUMENTS

| DE | 19846630 A1 | 4/2000 |
| EP | 1527740 A1 | 5/2005 |

(Continued)

OTHER PUBLICATIONS

The International Search Report and Written Opinion dated Jun. 13, 2014 from corresponding PCT Application No. PCT/US2014/20323 filed on Mar. 4, 2014.

(Continued)

*Primary Examiner* — Katherine M Shi
(74) *Attorney, Agent, or Firm* — Seager, Tufte & Wickhem, LLP

(57) ABSTRACT

A catheter system includes an inflatable structural balloon and collapsible filter. The collapsible filter is deployable into an expanded configuration using the inflatable distal balloon. In the expanded configuration, one or more flow cells are formed between inflated portions of the balloon to provide continuous fluid flow between proximal and distal ends of the structural balloon. In the expanded configuration, the filter is configured to prevent particulates (e.g., dislodged thrombus, or other particulate material) from migrating beyond the filter. In the expanded configuration, the inflated structural balloon biases a perimeter of the filter toward or against a subject vessel wall.

12 Claims, 7 Drawing Sheets

(56) References Cited

U.S. PATENT DOCUMENTS

| | | | |
|---|---|---|---|
| 7,722,634 | B2 | 5/2010 | Panetta et al. |
| 7,846,175 | B2 | 12/2010 | Bonnette et al. |
| 2001/0007947 | A1 | 7/2001 | Kanesaka |
| 2003/0028238 | A1 | 2/2003 | Burkett et al. |
| 2005/0038468 | A1* | 2/2005 | Panetta et al. ............ 606/200 |
| 2005/0119691 | A1 | 6/2005 | Daniel et al. |
| 2006/0129091 | A1 | 6/2006 | Bonnette et al. |
| 2006/0129180 | A1 | 6/2006 | Tsugita et al. |
| 2008/0097294 | A1 | 4/2008 | Prather et al. |
| 2008/0275393 | A1 | 11/2008 | Bonnette et al. |
| 2012/0109179 | A1 | 5/2012 | Murphy et al. |

FOREIGN PATENT DOCUMENTS

| | | |
|---|---|---|
| EP | 2241284 A1 | 10/2010 |
| WO | 9838920 A1 | 9/1998 |
| WO | 98/51237 A1 | 11/1998 |
| WO | 9916382 A2 | 4/1999 |
| WO | 01/49209 A1 | 7/2001 |
| WO | 01/70325 A2 | 9/2001 |
| WO | 20080117256 | 10/2008 |
| WO | 20080117257 | 10/2008 |

OTHER PUBLICATIONS

Office Action dated Apr. 24, 2017 from Chinese Patent Application No. 201480026679.X.

\* cited by examiner

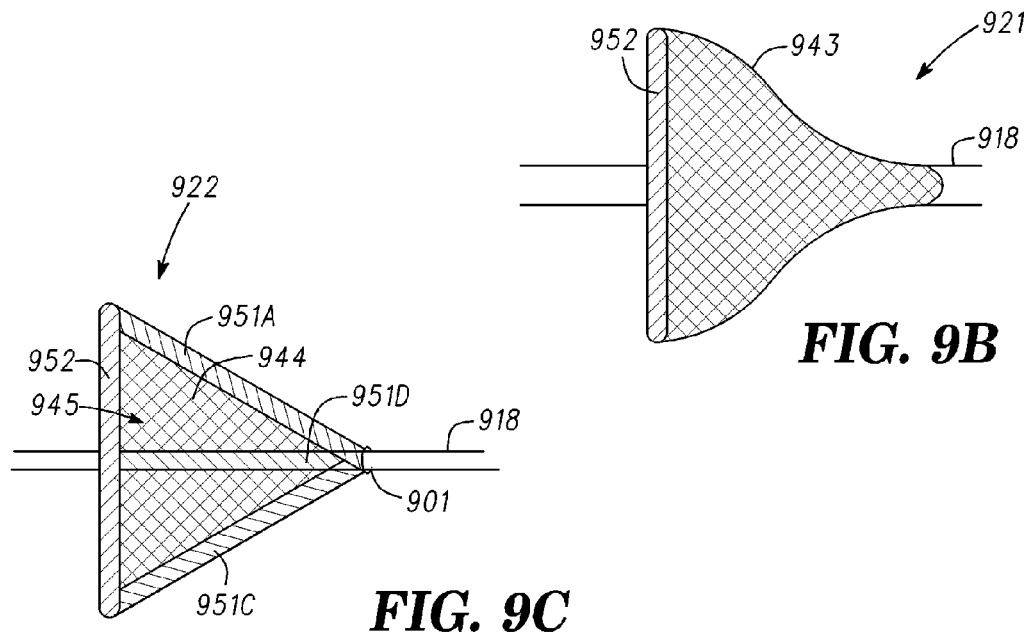
FIG. 9B
FIG. 9C
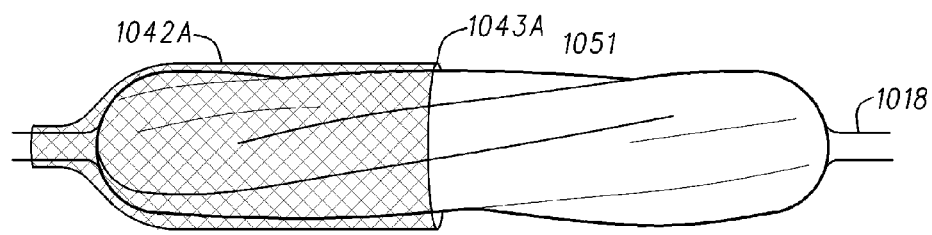
FIG. 10A
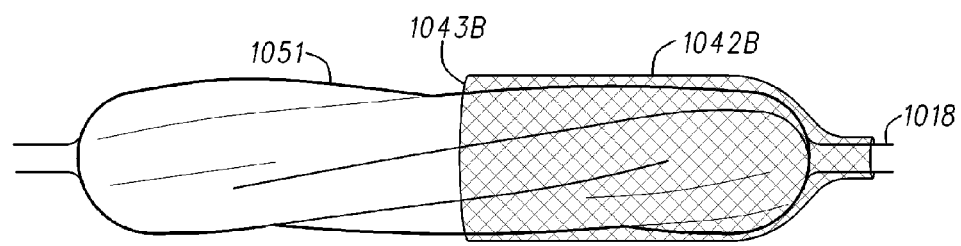
FIG. 10B

CATHETER SYSTEM WITH BALLOON-OPERATED FILTER SHEATH AND FLUID FLOW MAINTENANCE

TECHNICAL FIELD

This document pertains generally, but not by way of limitation, to catheter systems having a distal balloon configured to deploy one or more implements in a subject vessel.

BACKGROUND

Blood vessels become plugged with thrombus or plaque that may ultimately lead to ischemia, a substantial reduction or loss of blood flow to body tissue. A variety of vascular medical devices and procedures have been developed to treat diseased or clogged vessels, including surgical procedures (e.g., bypass surgery where a new blood vessel is grafted around a narrowed or blocked artery), and nonsurgical interventional vascular medical procedures, including angioplasty (where a balloon is inflated inside a narrowed or blocked portion of an artery in an attempt to compress plaque or thrombotic material), stenting (where a metal mesh tube is expanded against a narrowed or blocked portion of an artery to compress plaque or thrombotic material against a vessel wall), and debulking techniques in the form of atherectomy (where a mechanical mechanism dislodges hardened plaque) or thrombectomy (where a mechanical or hydrodynamic mechanism dislodges thrombotic material). In at least some of these interventional vascular medical procedures, a flexible guidewire is routed through the vascular system to a treatment location, and a catheter that includes a distally mounted device appropriate for the given procedure is tracked along the guidewire to the treatment location.

Although interventional vascular procedures avoid many of the complications involved in surgery, there is a possibility of complications if some of the plaque, thrombus or other material breaks free and flows downstream in the artery or other vessel, potentially causing a stroke, a myocardial infarction (heart attack), or other tissue death. One solution to this potential complication is to use an occlusive device or filtering device to block or screen blood from flowing downstream of the treatment location.

In some examples, a protective device such as a balloon can be used. Use of a protective device in conjunction with an atherectomy or thrombectomy device is intended to prevent particulate matter from migrating beyond the protective device and to allow removal of the particulate matter. The balloon is inserted and inflated at a point downstream to the treatment site or lesion site. Therapy is then performed at the site and the balloon acts to block blood flow, which prevents particulate matter from traveling beyond the balloon. Following treatment, some form of particulate removal device is used to remove the dislodged particulates prior to balloon deflation.

Other devices screen blood through a filter arrangement, or strainer. In an example, a strainer device is inserted into a vessel and actuated via a control cable to open and close tines capable of retaining dislodged particulate matter. After treatment, the strainer device is collapsed and the retained particulate matter is removed from the body. In some examples, a nitinol mesh filter is used, or a collapsible filter exhibiting shape memory is used. Such filters are removed by reshaping the collapsible filter, such as by contracting peripheral edges of the filter toward a guidewire, thus reducing a cross section of the filter. In some examples, removal can be via a delivery sheath or other catheter.

OVERVIEW

The present inventor has recognized, among other things, that a problem to be solved can include executing medical procedures in a subject vessel without occluding or stopping blood flow through the vessel while at the same time preventing the downstream migration of particulate. The present inventor has recognized that a further problem to be solved includes using a catheter system to provide a distal filter with improved apposition to, or engagement with, a subject vessel wall.

In an example, the present subject matter provides a solution to these problems, such as by providing a catheter system with a filter sheath deployable by an inflatable structural balloon. While effective as a protective device, use of an occlusive balloon may result in damaged tissue due to lack of downstream blood flow, and filters generally suffer from complicated deployment structures and retraction schemes. Accordingly, in an inflated configuration, an example of the present subject matter includes one or more fluid passages extending from proximal to distal sides of a structural balloon such that blood flow is not occluded, while a filter sheath cooperates with the structural balloon to reliably capture particulate (and accordingly prevent downstream migration of particulate). The structural balloon can also improve apposition of the filter sheath to a vessel wall.

In an example, the filter sheath is coupled to the structural balloon. In a collapsed configuration, the filter sheath is collapsed around the structural balloon, and in an expanded configuration, the filter sheath is expanded according to inflation of the structural balloon (e.g., the filter sheath assumes a shape influenced by the inflated structural balloon). For example, the filter sheath is expanded by the structural balloon until a perimeter of the filter sheath is apposed with (e.g., touching) an inner wall of a vessel. In some examples, the structural balloon includes multiple inflatable portions that extend in different directions away from a central tube of the catheter system to form one or more flow cells between the inflatable portions. For example, the structural balloon includes multiple spokes that extend from the central tube to the vessel wall, and the flow cells extend along the balloon between the spokes. In other examples, the structural balloon is one or more of helical or conical, and a flow cell extends along a corresponding helical or conical path from a proximal end to a distal end of the structural balloon. Stated another way, the plurality of inflatable portions (e.g., ridges, helical portions and the like) of the structural balloon provide a plurality of locations for engagement with the filter sheath. As the structural balloon is inflated an outer edge (e.g., a perimeter) provided by the plurality of locations engaged with the filter sheath biases the filter sheath outwardly and causes the filter sheath to assume a shape corresponding to the outer edge, for instance a shape that annularly engages against the vessel wall while at the same time maintaining blood flow through the one or more flow cells.

Optionally, the filter sheath and structural balloon are collapsed, such as after a thrombectomy or other procedure, whereby particulate matter is collected by the filter sheath. In the collapsed configuration, particulate matter is entrapped, for example, between the filter sheath and the structural balloon, or between the filter sheath and the catheter tube. In one example, the particulate received within the one or more flow cells is clamped between the collapsed structural balloon and the filter sheath (collapsed by the balloon) and reliably retained therein. In an example, a recovery sheath is provided. The recovery sheath slides over the collapsed filter sheath to further entrap particulates, for instance, while the catheter system is withdrawn from the subject vessel. Stated another way, the combination of the collapsed structural balloon and filter sheath (and clamping engagement of the particulate) along with the recovery sheath provides a composite system that reliably captures and retains particulate matter during removal of the catheter system.

The structural balloon described herein is optionally used to deploy filters, stents, embolic coils, or other medical devices. In another example, the structural balloon is used as an angioplasty balloon to expand vessels while maintaining continuous blood flow through the treatment area (e.g., through the flow cells). In an example, a drug (e.g., lytics) is perfused into a treatment area or into a subject blood stream using one or more holes on the structural balloon, or on the catheter tube proximal to the structural balloon, to deliver the drug.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The disclosure may be more completely understood in consideration of the following detailed description of various embodiments of the disclosure in connection with the accompanying drawings, which are as follows.

FIG. 9B illustrates generally a side view of a first example of a catheter with a wheel balloon.

FIG. 9C illustrates generally a side view of a second example of a catheter with a wheel balloon.

FIG. 10A illustrates generally a side view of an extended spiral balloon with a convex filter.

FIG. 10B illustrates generally a side view of an extended spiral balloon with a concave filter.

DETAILED DESCRIPTION

Figure 1:
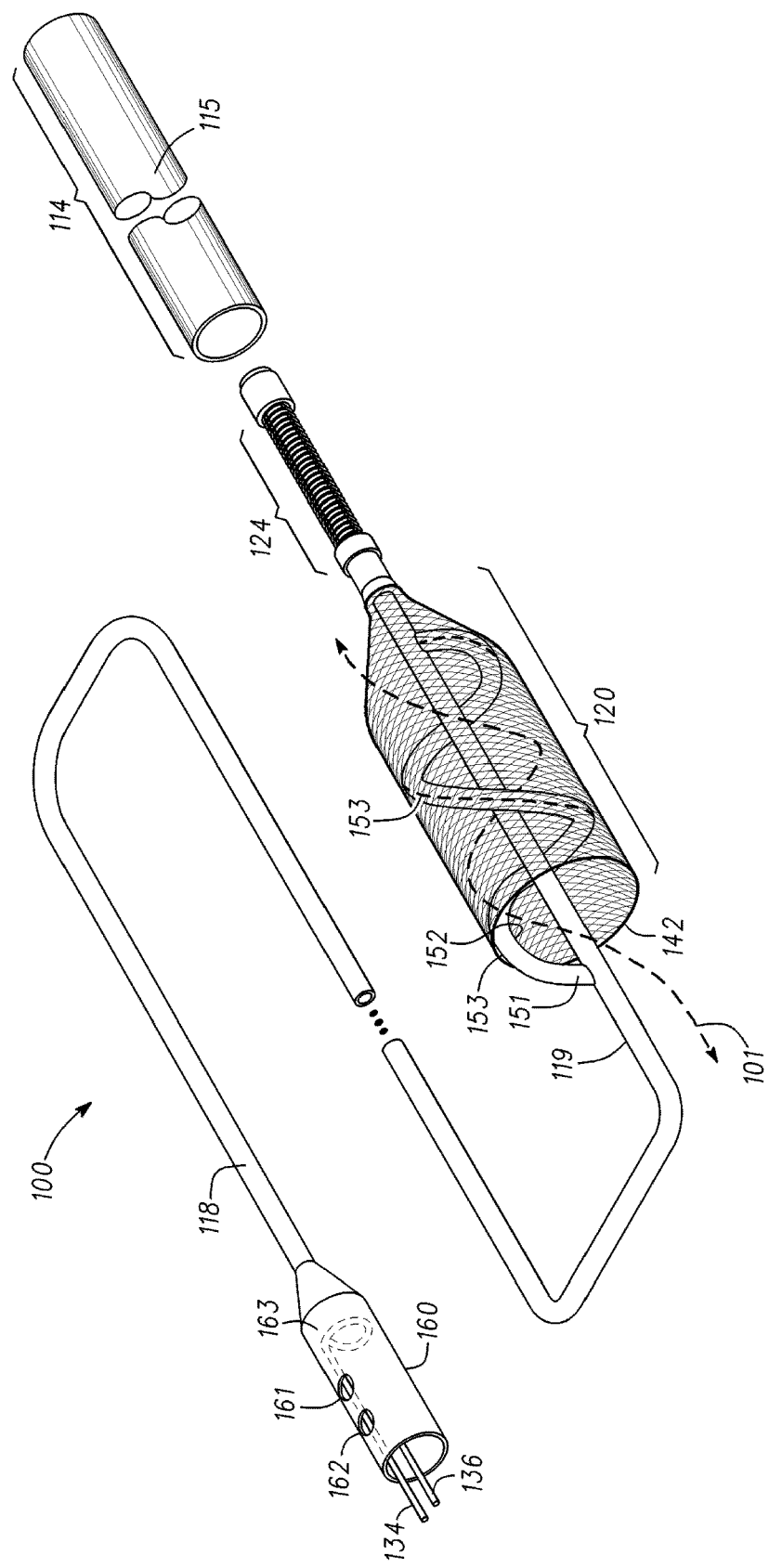
FIG. 1 is an exploded perspective view showing a portion of a catheter system with a non-occlusive inflatable balloon and collapsible filter.

FIG. 1 is an exploded perspective view showing a portion of a catheter system 100 with a collapsible filter system 120. The collapsible filter system 120 includes a non-occlusive inflatable balloon 151 and collapsible filter 142 positioned on a guidewire 118 of the catheter system 100. The catheter system 100 further includes a flexible tip 124, and a delivery/recovery sheath 114 having a lumen 115, and a catheter 160. The catheter 160 includes a fluid emanator 163 supplied by an infusion tube 134. The catheter 160 further includes inflow and outflow orifices 161, 162 to provide a recirculating flow of fluid provided by the fluid emanator 163, such as to forcibly dislodge thrombus near the catheter 160 and collect dislodged thrombus using the inflow orifice 161.

In an example, the catheter system 100 includes a cross-stream, cross flow, or rheolytic thrombectomy catheter such as described by Bonnette et al., in U.S. Patent Publication No. 2006/0129091, entitled "ENHANCED CROSS STREAM MECHANICAL THROMBECTOMY CATHETER WITH BACKLOADING MANIFOLD," or by Bonnette et al., in U.S. Pat. No. 6,676,637, entitled "SINGLE OPERATOR EXCHANGE FLUID JET THROMBECTOMY METHOD," which are hereby incorporated herein by reference in their entirety.

In an example, the collapsible filter system 120 is positioned to collect dislodged thrombus or other particulate matter flowing downstream from the catheter 160. In another example, the collapsible filter system 120 is mounted on a catheter, and in another example, the guidewire 118 with the collapsible filter system 120 is slidably received within a thrombectomy catheter (e.g., the catheter 160) or other treatment catheter.

The catheter system 100 further includes a balloon supply tube 136 and a fluid supply tube 134, one or both of which can extend from proximal to distal portions of the guidewire 118. In an example, the fluid supply tube 134 is coupled to a distal fluid jet emanator positioned on the guidewire 118 proximal to the collapsible filter system 120. In an example, the balloon supply tube 136 is coupled to the non-occlusive inflatable balloon 151. A proximal end of the guidewire 118 is optionally coupled to a user interface device, such as a handheld control mechanism that includes one or more controls for, among other things, steering a distal portion of the guidewire 118, or actuating the collapsible filter system 120, such as by adjusting fluid (e.g., gas, liquid) supply to the balloon 151.

In the example of FIG. 1, the collapsible filter system 120 includes the inflatable balloon 151 (shown in an inflated configuration) and collapsible filter 142, and the collapsible filter system 120 is positioned on the guidewire 118 near a distal end of the guidewire 118. In an example, the collapsible filter 142 is expandable according to inflation of the balloon 151, and, in some examples, is biased toward an open filter configuration when the balloon 151 is pressurized. That is, when inflated, the balloon 151 acts as a structural support for the expanded collapsible filter 142. In an expanded configuration (i.e., inflated), the balloon 151 is non-occlusive to fluid flow when the balloon 151 is deployed in vessels of sufficient diameter. That is, where a clearance exists between an outer portion of the guidewire 118 and an inner wall of a vessel, the balloon 151 expands to provide one or more flow cells that extend along one or more inflated portions of the balloon 151. The one or more flow cells, as further described herein, provide continuous fluid communication between proximal and distal ends of the balloon 151 and the collapsible filter system 120.

In the example of FIG. 1, the collapsible filter 142 is coupled to the balloon 151 and to the guidewire 118 distal to the balloon 151. The collapsible filter 142 is deployed according to expansion of the balloon 151 such that particulate matter (e.g., thrombus, lesions, clots, plaque, or other deposits or debris) flowing through the one or more flow cells is captured by the collapsible filter 142. In an example, the collapsible filter 142 is porous and allows some vascular fluid (e.g., natural bodily fluids including blood, contrast fluids, or the like) to pass through the filter 142. Accordingly, in the expanded configuration, blood or other fluids flow through the one or more flow cells provided by the inflated balloon 151 and continue through the vessel, such as during a thrombectomy procedure. Thrombus or other particulate matter is captured and prevented from flowing downstream by the collapsible filter 142. In an example, thrombectomy or other procedures are performed in combination with injected contrast media while using the catheter system 100 because fluid flow is maintained through the vessel.

The balloon 151 and the collapsible filter 142 can take on many different configurations and shapes, as described herein. The examples of balloons and filters provided in the figures are provided as example configurations, and other configurations are within the scope of this disclosure and the appended claims. In the example of FIG. 1, the balloon 151 has a spiral or helical shape. That is, a proximal end of the balloon 151 is coupled with a first portion of the guidewire 118, and a distal end of the balloon 151 is coupled with a second portion of the guidewire 118 that is distal to the first portion. As shown in FIG. 1, the spiral balloon 151 is wrapped around the guidewire 118 (e.g., approximately 720 degrees, in the example of FIG. 1). In an example, at least one of the ends of the balloon 151 is coupled to the balloon supply tube 136 to receive fluid for inflation (and alternatively a negative pressure for deflation). The spiral balloon 151 is coupled with the guidewire 118 at one or more points where the balloon 151 crosses the guidewire 118. In some examples, an inner edge 152 of the spiral balloon 151 is continuously apposed with (i.e., touching or pressed against) an outer edge 119 surface of the guidewire 118, such as along all or a portion of the length of the spiral balloon 151. As shown in FIG. 1, the balloon 151 is tubular, and the inner edge 152 of the balloon 151 is spaced from the outer edge 119 surface of the guidewire 118 (excepting the junctions coupled with the guidewire such as the proximal and distal balloon ends).

In the example of FIG. 1, a flow cell (denoted by the dashed line 101) includes at least the areas between the guidewire 118, the spiral balloon 151, and the collapsible filter 142 that, in situ, are otherwise filled will blood, other fluids, particulate matter, or the like. That is, the flow cell provides a flow path that extends along the guidewire 118, around the inflated balloon 151, and through the collapsible filter 142. In an example, a portion of the collapsible filter 142 is a hollow cylindrical sheath, such as having an outer wall that is apposed with an inner vessel wall. The inflated balloon 151 can include an outer edge, or a continuous apex 153, that is continuously apposed with at least a portion of the inner wall of the cylindrical portion of the collapsible filter 142 along a longitudinal axis of the cylinder, and the guidewire 118 can extend along the longitudinal axis of the cylindrical. The remaining volume of the cylindrical portion of the collapsible filter 142 includes the flow cell, which provides uninterrupted fluid communication between proximal and distal ends of the balloon 151. That is, a flow cell provides substantially non-occluded fluid path, or passage, that extends along the longitudinal axis of the cylinder (e.g., corresponding to a longitudinal axis of the guidewire 118).

In an example, an inner portion of the collapsible filter 142 is engaged with, or affixed to, the apex 153 of the balloon 151, for instance, with one or more of glue, heat bonds, welds (e.g., ultrasonic welds), or the like. Because the collapsible filter 142 is coupled with the balloon 151, the collapsible filter 142 expands (and optionally contracts) according to inflation of the balloon (or deflation for contraction). In some examples, the collapsible filter 142 is sufficiently elastic such that nearby portions of the filter coupled to adjacent portions of the balloon 151 stretch as the balloon 151 inflates. Alternatively or additionally, the collapsible filter 142 is corrugated or bunched, in the collapsed configuration (e.g., like a collapsed umbrella). Accordingly, as the balloon 151 inflates toward the expanded configuration, the corrugates of the collapsible filter 142 open and spread apart (e.g., like an expanding umbrella). Conversely, when the balloon 151 deflates, the collapsible filter 142 (e.g., coupled along the balloon apex 153) is pulled or collapsed toward the central guidewire 118 by the balloon 151. In other examples, the collapsible filter 142 is unattached to the balloon 151, or "floats." That is, the collapsible filter 142 expands according to inflation of the balloon 151, but may need to rely on another mechanism (such as the delivery/recovery sheath 114) to collapse the filter. Optionally, a cord is used to cinch shut the collapsible filter 142, such as described by Bonnette et al., in U.S. Pat. No. 7,846,175, entitled "GUIDEWIRE AND COLLAPSABLE FILTER SYSTEM," which is hereby incorporated herein by reference in its entirety. Whether the collapsible filter 142 is floating or fixedly coupled to the balloon 151, forcible elongation and reduction of the profile of the collapsible filter 142 (e.g., by virtue of the deflating balloon 151, the cinch, or another mechanism), particulate matter can be captured and optionally compacted by the diminishing profile of the collapsible filter 142.

The balloon 151 is constructed with materials that are noncompliant, semi-compliant, or compliant, such as including Pellethane 2363 80AE (a type of polyurethane), silicone, or Pebax, among other materials. In an example, in the expanded or inflated configuration, the balloon 151 has an outer edge diameter between about 2 mm and 20 mm, such as at a pressure up to about 20 ATM. The collapsible filter 142 includes a flexible material, including, but not limited to, a Nitinol mesh, a porous sponge or foam sheet, a porous polymer sheet (e.g., comprising multiple laser-drilled holes), a weaved polymer, or a weaved composite metal polymer, among other materials.

In an example, the balloon 151 is coupled to a distal portion of the balloon supply tube 136, and the balloon 151 is controllably inflated or deflated according to an automatic or user control provided at a proximal end of the balloon supply tube 136, such as using an appropriate user interface or control mechanism. Examples of an air supply control mechanism are described in Prather et al., U.S. Patent Publication No. 2008/0097294, entitled "OCCLUSIVE GUIDEWIRE SYSTEM HAVING AN ERGONOMIC HANDHELD CONTROL MECHANISM PREPACKAGED IN A PRESSURIZED GASEOUS ENVIRONMENT AND A COMPATIBLE PREPACKAGED TORQUEABLE KINK-RESISTANT GUIDEWIRE WITH DISTAL OCCLUSIVE BALLOON," which is hereby incorporated herein by reference in its entirety. In an example, the proximal end of the balloon supply tube 136 is coupled to a pressurized, adjustable gas source, such as a $CO_2$ source. In some examples, the balloon 151 can be controllably deflated with the controlled application of a negative pressure (e.g., a vacuum), such as coupled to the balloon supply tube 136. In an example, a separate vacuum supply tube is coupled to the balloon 151. In some examples, the balloon 151 is deflated by cutting (e.g., severing) the balloon supply tube 136, for instance at the proximal portion of the guidewire 118, using scissors or another appropriate cutting tool.

In an example, the balloon 151 is coupled to a distal portion of the fluid supply tube 134, and the balloon 151 is controllably inflated or deflated according to an automatic or user control provided at a proximal end of the fluid supply tube 134. For example, the proximal end of the fluid supply tube 134 is coupled to a pressurized fluid source, and the balloon 151 is controllably inflated or deflated according to control of the fluid source pressure. One or both of the fluid supply tube 134 or the balloon supply tube 136 can be flexible and crimpable, and can be comprised of, among other materials, metals, plastics, composites, or the like. The crimpable tubes are designed to be repeatably sealed using respective sealing mechanisms that can crimp together opposite sides of the tubes.

Figure 2:
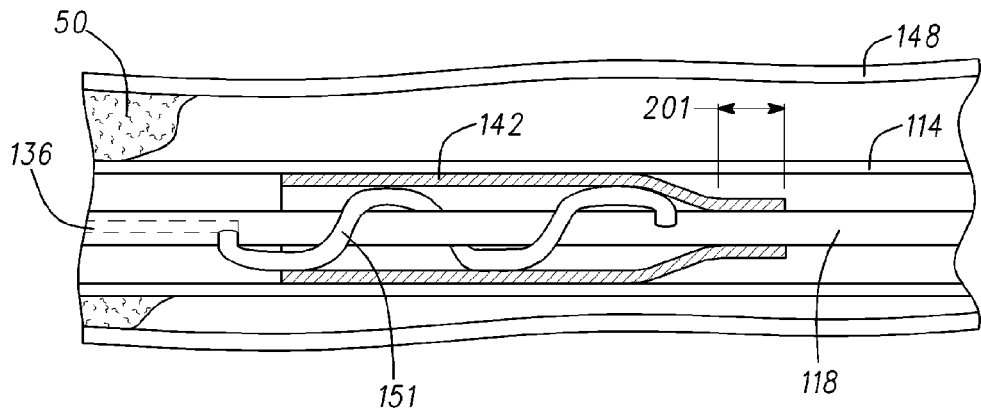
FIG. 2 is a partial cross section view showing a distal portion of a catheter system with an inflatable balloon and collapsible filter in a collapsed configuration in a subject vessel.

FIGS. 2, 3, 4, and 5, illustrate generally an example of an operating mode of the catheter system 100. Referring now to FIG. 2, a partial cross section view of a distal portion of the catheter system 100 is shown with the collapsible filter system 120 in a collapsed (i.e., non-inflated) configuration and in a subject vessel. The subject vessel includes the vessel wall 148, and the collapsible filter system 120 is positioned inside the vessel along a longitudinal axis of the vessel. In the example of FIG. 2, the distal portion of the catheter system 100, including the delivery/recovery sheath 114 and the collapsible filter system 120, is positioned slightly beyond, or distal to, a vessel blockage site including thrombus 50.

In the example of FIG. 2, the delivery/recovery sheath 114 is provided around the collapsible filter system 120, retaining the collapsible filter system 120 in a minimized profile for delivery of the collapsible filter system 120 to or near a therapy site. The minimized profile includes, for example, the balloon 151 deflated, and the collapsible filter 142 constricted about the guidewire 118. In some examples, in the collapsed configuration, at least a portion of the collapsible filter 142 surrounds the deflated balloon 151.

FIG. 2 illustrates generally the collapsible filter 142 optionally coupled to the guidewire 118 along a distal end 201 of the collapsible filter system 120. As further described herein, the collapsible filter 142 is coupled to the balloon 151, and is optionally further coupled to the guidewire 118, such as proximal or distal to the balloon 151, or both.

Figure 3:
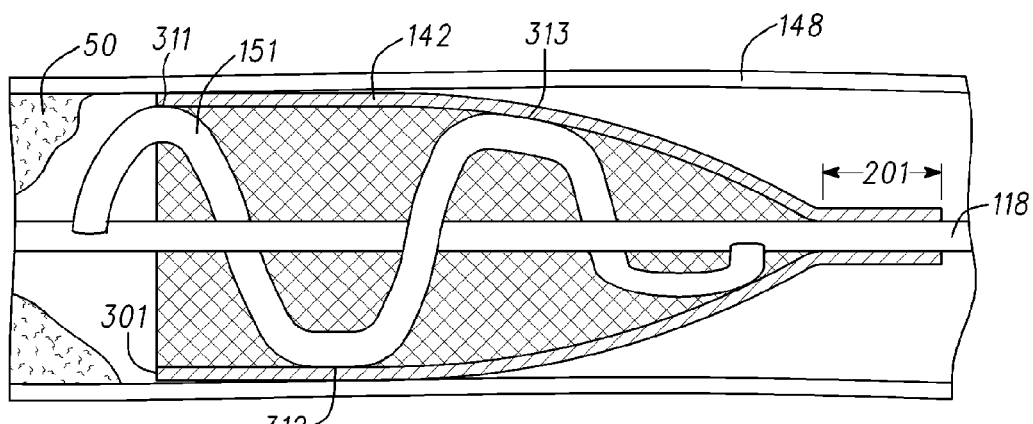
FIG. 3 is a partial cross section view showing a distal portion of a catheter system with an inflatable balloon and collapsible filter in an expanded configuration in a subject vessel.

FIG. 3 shows a partial cross section view of a distal portion of the catheter system 100 with the collapsible filter system 120 in an expanded configuration and in the subject vessel. That is, FIG. 3 shows the collapsible filter system 120, as shown in FIG. 1, deployed in a subject vessel. In the example of FIG. 3, the balloon 151 is inflated and extends radially away from the guidewire 118 toward the vessel wall 148. The collapsible filter 142 is interposed between the balloon 151 and the vessel wall 148. As previously described, the collapsible filter 142 is coupled to the balloon 151, such as along all or a portion of an outer edge of the balloon 151 (e.g., along the apex 153). For example, in the cross section shown in FIG. 3, the collapsible filter 142 is coupled to the balloon 151 at least at a first point 311, a second point 312, and a third point 313. In three dimensional space the collapsible filter 142 is coupled to the balloon 151 along all or a portion of a continuous curve that extends along an outer surface of the balloon 151 connecting, for example, the first and second points 311 and 312, the second and third points 312 and 313, and so on.

As shown in the example of FIG. 3, a proximal end 301 of the collapsible filter 142, near a proximal end of the balloon 151, is substantially apposed with the vessel wall 148. Because the balloon 151 is spiral shaped, a continuous edge of the collapsible filter 142 overlying the balloon 151 is biased toward and against the vessel wall 148. Accordingly, the proximal end 301 of the collapsible filter 142 forms a mouth configured to receive substantially all of the fluid or other material passing through the vessel and filter that fluid as described herein. More distally, the collapsible filter 142 follows a tapering contour of the inflated balloon 151 and terminates at the distal end 201 of the collapsible filter system 120 (e.g., at the guidewire 118). In this manner, all flow through the vessel bounded by the vessel wall 148 is passed around the balloon 151 and filtered using the collapsible filter 142 in the expanded configuration.

Figure 4:
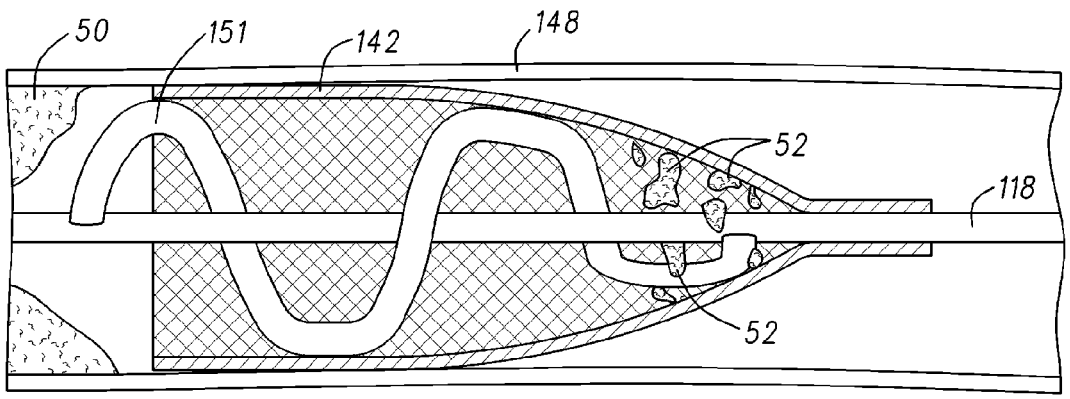
FIG. 4 is a partial cross section view showing a distal portion of a catheter system with an inflatable balloon and collapsible filter subsequent to filtration of thrombotic particulate by the filter.

Referring now to FIG. 4, the catheter system 100 of FIG. 3 is shown subsequent to filtration of particulate matter 52 by the collapsible filter 142. As described above, in an example, the collapsible filter system 120 is deployed distal to the thrombus 50. One or more fluid jet emanators, such as included in the catheter 160 of FIG. 1, among other devices configured to break up or dislodge the thrombus 50, can be provided using the catheter system 100 or another system. As shown, dislodged or broken up thrombus, in the form of the particulate matter 52, flows along the vessel and passes the expanded portions of the balloon 151. The tapered configuration of the collapsible filter 142 guides the particulate matter 52 to collect near the distal end 201 of the collapsible filter 142, as shown in FIG. 4.

Figure 5:
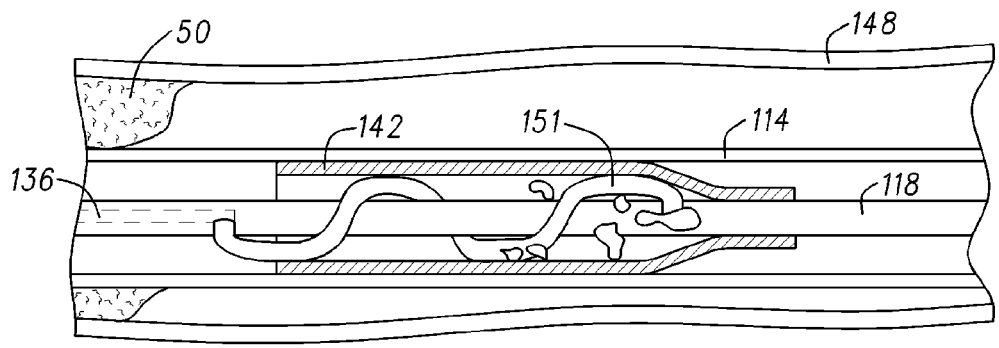
FIG. 5 is a partial cross section view showing a distal portion of a catheter system with an inflatable balloon and collapsible filter in a collapsed configuration after filtration of thrombotic particulate by the filter.

The balloon 151, shown in the expanded or inflated configuration in FIG. 4, is deflatable to return the catheter system 100 to a diminished profile, such as similar to the profile shown in the example of FIG. 2. When the balloon 151 deflates, the collapsible filter 142 is drawn radially inward, toward the guidewire 118, to capture and retain the particulate matter 52 inside of the collapsible filter 142. In an example, the balloon 151 is coupled to the collapsible filter 142 (e.g., along the apex 153 of the balloon 151, shown in FIG. 1), and therefore changes in the profile of the balloon 151 translate to similar changes in an outer profile of the filter 142. FIG. 5 shows the collapsed configuration of the catheter system 100, such as after the balloon 151 is deflated.

FIG. 5 is a partial cross section view showing a distal portion of the catheter system 100 after filtration of particulate matter 52 and in preparation for withdrawal from the subject vessel. The example of FIG. 5 corresponds to the example of FIG. 2, however the example of FIG. 5 illustrates that the particulate matter 52 is trapped between the collapsible filter 142 and the guidewire 118.

In an example, a negative pressure is applied to the balloon 151 to deflate the balloon from the expanded configuration of FIG. 4 to the collapsed configuration of FIG. 5. In some examples, the negative pressure is supplied by a vacuum coupled to the balloon supply tube 136. The vacuum optionally supplies a sufficient negative pressure to compress the captured particulate matter 52, using the collapsible filter 142, against the guidewire 118 and deflated portions of the balloon 151. The negative pressure on the balloon 151 further diminishes an overall profile of the collapsible filter system 120, for instance, so that the delivery/recovery sheath 114 may be withdrawn over the collapsible filter system 120. The delivery-recovery sheath 114 optionally further compresses the collapsible filter system 120.

Figure 6:
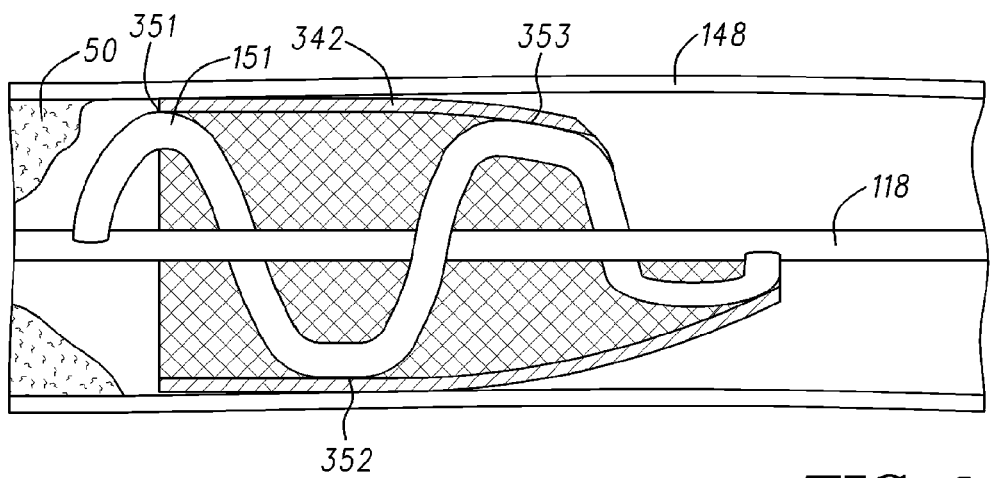
FIG. 6 is a partial cross section view showing a distal portion of a catheter system with an inflatable balloon and collapsible filter in an expanded configuration in a subject vessel.

FIG. 6 shows a partial cross section view of a distal portion of a catheter system with the balloon 151 and an alternate collapsible filter 342 in an expanded configuration in a subject vessel. In the example of FIG. 6, the alternate collapsible filter 342 is coupled to the balloon 151 at several points (e.g., at points 351, 352, 353, etc., instead of or in addition to being coupled with the balloon 151 at the apex 153, shown in the example of FIG. 1). Instead of terminating at the guidewire 118 (as in the previous embodiment), the alternate collapsible filter 342 follows the contours of the balloon 151 up to the guidewire 118. In this manner, the volume of material used to provide the alternate collapsible filter 342 is reduced relative to the collapsible filter 142. Reducing the volume of the filter further reduces a cross-sectional area of the collapsible filter system 120, and in some examples reduces an outer diameter of the overall catheter system that uses the collapsible filter system 120.

FIGS. 7A through 10D illustrate generally several examples of balloon and filter system configurations. Each of the example systems is operable in collapsed and expanded configurations as described above with respect to the example of the spiral or helical balloon 151. That is, each example is deployable in a subject vessel in a collapsed configuration, expandable to facilitate filtering of particulate matter flowing through the vessel, such as during a thrombectomy or other procedure, and then collapsible to collect the filtered particulate matter for withdrawal from the subject vessel.

Figure 7A:
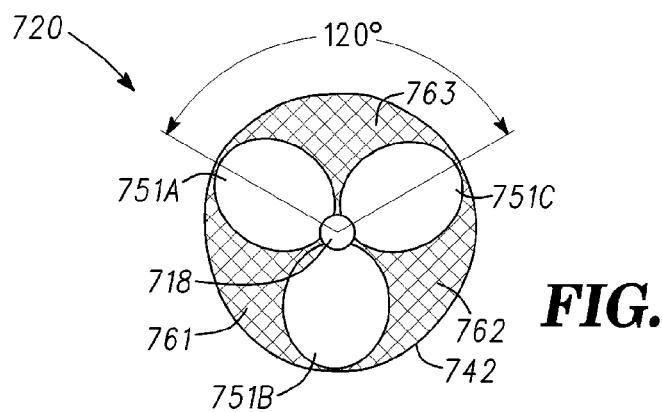
FIG. 7A illustrates generally an end view of an example of a catheter with multiple staggered balloons.
Figure 7B:
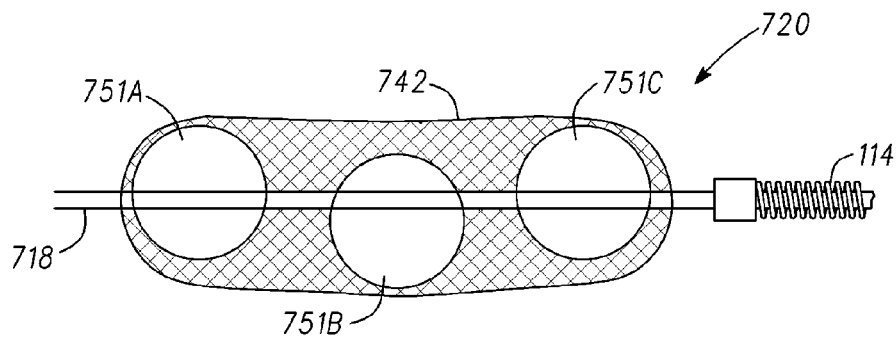
FIG. 7B illustrates generally a side view of an example of a catheter with multiple staggered balloons.

FIG. 7A illustrates generally an end view of an example of a catheter including a collapsible filter system 720 with multiple staggered balloons 751A, 751B, and 751C. FIG. 7B illustrates generally a longitudinal side view of the collapsible filter system 720 with the staggered balloons. As few as two balloons are used in similar examples, or greater than three balloons are used in still other examples. The collapsible filter system 720 includes a guidewire 718, and the multiple staggered balloons 751A, 751B, and 751C are positioned at different locations along the guidewire 718. In an example, each of the multiple staggered balloons 751A, 751B, and 751C is configured to extend away from the guidewire 718 in a substantially different radial direction. In the example of FIG. 7A, the multiple staggered balloons 751A, 751B, and 751C are offset around the guidewire 718, such that the second and third balloons 751B and 751C are spaced from the first balloon 751A by about 120 degrees. That is, in the example of FIGS. 7A and 7B, the multiple staggered balloons 751A, 751B, and 751C have respective axes that extend from origins (e.g., a common origin) at or near the guidewire 718 through respective balloon diameters and balloon apexes such that the axes of the respective balloons are spaced about 120 degrees apart around the guidewire 718. The balloon apexes are the points on the balloons 751A, 751B, and 751C that are most distant from a central axis of the guidewire 718. In other examples, the staggered balloons 751A-C are positioned around the guidewire 718 at other radial positions (e.g., every 30 degrees, 90 degrees or the like) with optional additional balloons.

The collapsible filter system 720 includes a collapsible filter 742. As described above in the discussion of FIGS. 1 through 6, the collapsible filter 142 is optionally coupled to the balloon 151. Similarly, the collapsible filter 742 is optionally coupled to any one or more of the balloons 751A, 751B, and 751C. For example, the collapsible filter 742 is coupled with the balloons 751A, 751B, and 751C, at their respective apexes. The collapsible filter 742 is coupled to proximal or distal ends of the guidewire 718, such as adjacent to the first and third balloons 751A and 751C, respectively. In an example, the various portions of the collapsible filter 742 have differing porosities, such as described below in the examples of FIGS. 10A through 10D.

In the example of FIGS. 7A and 7B, and most visibly shown in FIG. 7A, one or more flow cells are provided between adjacent balloons. For example, a first flow cell 761 is provided between the first and second balloons 751A and 751B, a second flow cell 762 is provided between the second and third balloons 751B and 751C, and so on. That is, the first flow cell 761 includes the area bound by the lower-left edge of the first balloon 751A, the upper-left edge of the second balloon 751B, and the collapsible filter 742. The second and third flow cells 762 and 763 are similarly formed with respect to their respective adjacent balloons. The flow cells 761, 762, or 763, provide continuous fluid communication between proximal and distal ends of the collapsible filter system 720, such as by extending between or around the multiple staggered balloons 751A, 751B, and 751C, along the length of the collapsible filter system 720.

In an example, the multiple staggered balloons 751A, 751B, and 751C, comprise a structural balloon, wherein the multiple staggered balloons 751A, 751B, and 751C, are each inflated portions of the structural balloon. That is, the multiple staggered balloons 751A, 751B, and 751C, structurally support the collapsible filter 742 when it is expanded or biased toward a subject vessel wall. In an example, increasing a number of balloons staggered along the guidewire 718 in the collapsible filter system 720 improves apposition of the collapsible filter 742 with the subject vessel. Optionally, other collapsible filter shaping or biasing members are used, such as a spring, or Nitinol filter members having shape memory, to further improve apposition of the collapsible filter 742 with the subject vessel, such as in regions of the collapsible filter 742 between adjacent balloons. Although the example of FIGS. 7A and 7B shows balloons that are generally spherical, the multiple staggered balloons 751A, 751B, and 751C, can have other shapes, such as ellipsoids, cones, cylinders, and the like.

As shown in FIG. 7B, the multiple staggered balloons 751A, 751B, and 751C are discrete balloons that are each inflatable using a designated or common fluid supply (e.g., supplied using the balloon supply tube 136). In another example, one or more adjacent balloons are in direct fluid (gas) communication with each other, for instance, such that the balloons abut one another and, for example, no portion of the guidewire 718 is exposed between the balloons.

Figure 8A:
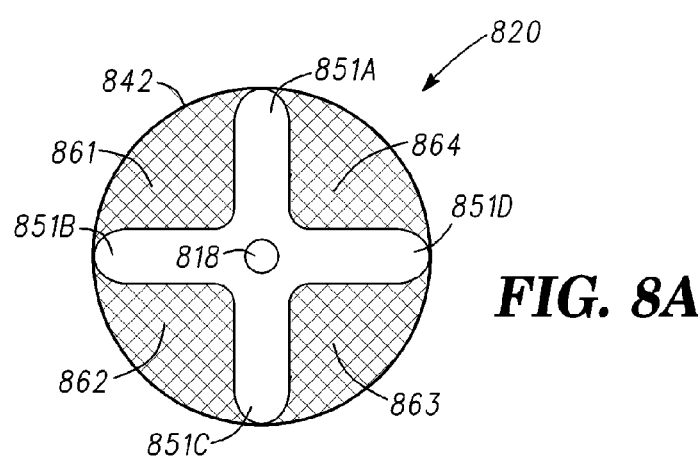
FIG. 8A illustrates generally an end view of an example of a catheter with a multi-arm balloon.
Figure 8B:
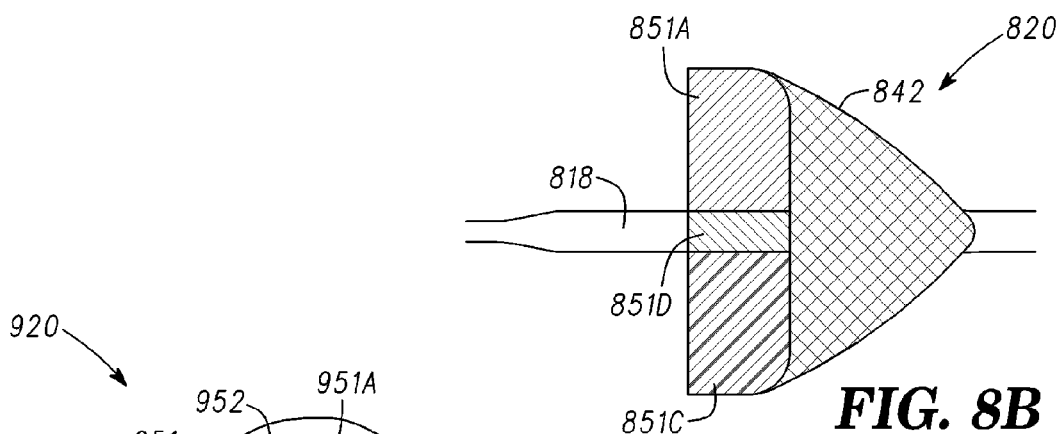
FIG. 8B illustrates generally a side view of an example of a catheter with a multi-arm balloon.

FIG. 8A illustrates generally an end view of an example of a catheter including a collapsible filter system 820 with a cross-shaped balloon 851. FIG. 8B illustrates generally a longitudinal side view of the collapsible filter system 820 with the cross-shaped balloon 851. The collapsible filter system 820 includes a guidewire 818 and a collapsible filter 842. The cross-shaped balloon 851 includes multiple inflatable portions (e.g., spokes or ridges that extend away from the guidewire 818). These inflatable portions are generally herein referred to as arms.

In the example of FIGS. 8A and 8B, the cross-shaped balloon 851 includes first, second, third, and fourth arms 851A, 851B, 851C, and 851D. Each of the first through fourth arms 851A-851D is configured to extend away from the guidewire 818 in different directions. That is, each of the balloon arms extends from respective origins at or near the guidewire 818, through respective balloon axes, and terminates at respective balloon apexes. In the example of FIGS. 8A and 8B, the adjacent portions of the cross-shaped balloon 851 are positioned around the guidewire 818 at approximately 90 degree intervals. As further shown in FIG. 8B, the first through fourth arms 851A-D extend longitudinally along the guidewire 818 to provide further support and stability to the arms while inflated, and bias the collapsible filter 842 outwardly.

The collapsible filter system 820 includes the collapsible filter 842. As described above in the discussion of FIGS. 1 through 6, the collapsible filter 142 is optionally coupled to the balloon 151. Similarly, the collapsible filter 842 is optionally coupled to the cross-shaped balloon 851 at any one or more of the first, second, third, and fourth arms 851A, 851B, 851C, and 851D. For example, the collapsible filter 842 is optionally coupled with the various portions at their respective apexes which are points spaced from the guidewire 818 (e.g., outlying points along each of the arms 851A-D).

In the example of FIGS. 8A and 8B, the collapsible filter 842 is coupled to the guidewire 818 distal to the cross-shaped balloon 851 in a configuration similar to that shown in the example of FIG. 1 with the spiral balloon 151. The collapsible filter 842 in this configuration acts like a net with an expandable mouth that is collapsible toward the guidewire 818 according to inflation and deflation of the cross-shaped balloon 851. In an example, the collapsible filter 842 is optionally coupled to the guidewire 818 proximal to the cross-shaped balloon 851 (see, e.g., the collapsible filter 742, of FIG. 7B, which is coupled to the guidewire 718) such that filter portions are provided proximal and distal to the cross-shaped balloon 851. The different filter portions optionally have different porosities, such as described below in the examples of FIGS. 10A through 10D, to facilitate passage of particulate matter into the filter 742 while preventing passage of the particulate out of the downstream portion of the filter.

In an example, the collapsible filter 842 is coupled to adjacent ones of the first, second, third, and fourth arms 851A, 851B, 851C, and 851D, of the cross-shaped balloon 851, such as without coupling to the guidewire 818. That is, the collapsible filter 842 includes multiple portions corresponding to the spaces between adjacent arms of the cross-shaped balloon 851. For example, a first portion of the collapsible filter 842 is coupled to the first and second arms 851A and 851B, a second portion of the collapsible filter 842 is coupled to the second and third arms 851B and 851C, and so on around the guidewire 818. In this manner, the collapsible filter 842 functions as a web, or fin, that is expandable and collapsible between adjacent supports.

In the example of FIGS. 8A and 8B, and most visibly shown in FIG. 8A, one or more flow cells 861-864 are provided between adjacent arms of the cross-shaped balloon 851. For example, a first flow cell 861 is provided between the first and second arms 851A and 851B, a second flow cell 862 is provided between the second and third arms 851B and 851C, and so on. That is, as shown in the example of FIG. 8A, the first flow cell 861 includes the area bound by the leftmost edge of the first arm 851A, the uppermost edge of the second arm 851B, and the collapsible filter 842. The second, third, and fourth flow cells 862, 863, and 864, are similarly formed with respect to their respective adjacent balloon arms. The flow cells 861-864 provide continuous fluid communication between proximal and distal ends of the collapsible filter system 820, such as by extending between or around the balloon arms 851A-851D along the length of the collapsible filter system 820. As discussed herein, fluid communication is maintained while particulate is captured by the filter 842.

In an example, the multiple balloon arms 851A-851D comprise a structural balloon, wherein the arms are each portions of the structural balloon. That is, the arms 851A-851D structurally support the collapsible filter 842 when it is expanded or biased toward a subject vessel wall. Optionally a greater number of balloon arms are provided in the collapsible filter system 820 to improve apposition of the collapsible filter 842 with the subject vessel. Although the example of FIGS. 8A and 8B shows balloon arms 851A-851D that are generally cylindrical or shaped like fins extending into the page (of FIG. 8A), the arms can have other shapes, such as spheres, ellipsoids, cones, and the like.

In an example, the arms of the cross-shaped balloon 851 are discrete balloons that are each inflatable using a designated or common air supply or fluid supply (e.g., supplied using the fluid supply tube 134 or the balloon supply tube 136). In some examples, the cross-shaped balloon 851 includes one or more adjacent balloons in direct fluid (gas) communication with each other, for instance, such that the balloons abut one another and no portion of the guidewire 818 is exposed. That is, in an example, the cross-shaped balloon 851 includes a single, cross-shaped or star-shaped balloon and the various arms or extending portions form a continuous, common air or fluid cavity.

In an example, multiple cross-shaped balloons are optionally provided at multiple locations along the guidewire 818. For instance, in the example of the collapsible filter system 720, the multiple staggered balloons 751A, 751B, and 751C, can each be a cross-shaped balloon, such as rotatably off-set from one another along the length of the collapsible filter system 720. Such a configuration yields improved apposition of the collapsible filter 742 with a subject vessel wall along the length of the collapsible filter system 720. In some examples, the arms of the cross-shaped balloon 851 may have bent limbs. That is, the arms extend radially away from the guidewire 818 toward a subject vessel wall using a first balloon portion, and, once impinged upon (or nearly impinged upon) the vessel wall, the arm extends substantially normally to the first balloon portion to follow a contour of the vessel wall. In some examples, the arms are "T" shaped, where the first balloon portion corresponds to the vertical base of the T, and the substantially normal extensions correspond to the horizontal cap of the T.

Figure 9A:
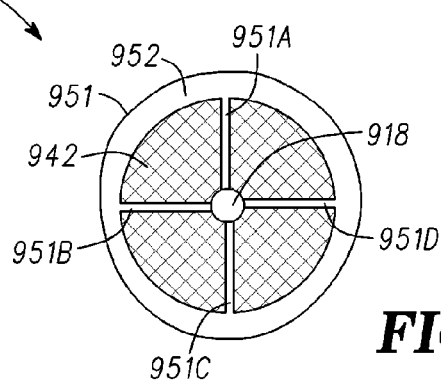
FIG. 9A illustrates generally an end view of an example of a catheter with a wheel balloon.

FIG. 9A illustrates generally an end view of an example of a catheter including a collapsible filter system 920 with a collapsible filter 942 and wheel shaped balloon 951. In this example, the balloon 951 includes multiple arms (e.g., 951A, 951B, 951C, and 951D) in communication with a peripheral torus 952. Although the example of FIG. 9A shows four arms 951A-D, the collapsible filter system 920 is optionally provided using more than four arms or as few as one arm.

In the example of FIG. 9A, the arms 951A-951D extend radially away from the guidewire 918 in differing directions. In the example of FIG. 9A, the adjacent arms are positioned around the guidewire 918 at approximately 90 degree intervals. In some examples, the arms extend radially away from the guidewire 918, toward the torus 952, in directions normal to the longitudinal axis of the guidewire 918 (see, e.g., FIG. 9B). In some examples, the arms extend away from the guidewire 918 at other angles (e.g., FIG. 9C).

In the example of FIG. 9A, the arms 951A-951D terminate at the torus 952, distal to the guidewire 918. The torus 952 is a substantially toroidal balloon portion that is substantially coaxial with the guidewire 918. Accordingly, when the balloon 951 is in the inflated configuration, the torus 952 expands and surrounds the guidewire 918 to provide one or more flow cells therebetween (in combination with the arms). The one or more flow cells comprise the open areas between the guidewire 918 and the torus 952, such as may be segmented into different flow cells by the arms 951A-951D.

Upon inflation, the torus 952 expands toward and engages a subject vessel wall. That is, when expanded, an outer edge (e.g., apex) of the torus 952 that is furthest away from the longitudinal axis of the guidewire 918 is apposed with the subject vessel wall. In some examples, the collapsible filter 742 is provided between the outer edge of the torus 952 and the subject vessel wall such that the torus 952 biases the collapsible filter 742 against the subject vessel wall.

In other examples, the collapsible filter 942 is coupled between adjacent ones of the first, second, third, and fourth arms 951A-951D, of the wheel balloon 951, and is optionally not coupled to the guidewire 918. That is, the collapsible filter 942 optionally includes multiple portions corresponding to the spaces bounded by the torus 952 and adjacent arms of the wheel balloon 951 (e.g., corresponding to each of the flow cells). For example, a first portion of the collapsible filter 942 is coupled to the first and second arms 951A and 951B and the torus 952, a second portion of the collapsible filter 942 is coupled to the second and third arms 951B and 951C and the torus 952, and so on around the guidewire 918.

FIG. 9B illustrates generally a longitudinal side view of a first configuration 921 of the collapsible filter system 920 with the wheel balloon 951. This first configuration 921 of the collapsible filter system 920 is expandable and collapsible according to inflation and deflation of the wheel balloon 951, such as described in the preceding examples. In the example of FIG. 9B, the arms 951A-951D extend radially away from the guidewire 918, toward the torus 952, in directions substantially normal to the longitudinal axis of the guidewire 918. That is, in the side view provided in FIG. 9B, the arms 951A-951D are not visible because they are positioned within the torus 952.

In the example of FIG. 9B, the first configuration 921 of the collapsible filter system 920 includes a collapsible filter 943 that is coupled to the wheel balloon 951 and to a portion of the guidewire 918 distal to the wheel balloon 951. In this example, the one or more flow cells from the example of FIG. 9A feed into a common net-like portion of the collapsible filter 943. Accordingly, in operation, thrombus or other particulate matter flows through the spaces between the arms 951A-951D and the torus 952 of the wheel balloon 951, and is collected by the net portion of the collapsible filter 943. In this configuration, particulate matter collects in the distal, tapered portion of the collapsible filter 943 (see, e.g., FIG. 4, where the particulate matter 52 is shown collected near a distal end of the collapsible filter system 120). Accordingly, when the filter 943 is collapsed with one or more of deflation of the balloon 951 or positioning of the sheath 114 the particulate is reliably captured within the filter 943 and removed.

FIG. 9C illustrates a longitudinal side view of a second configuration 922 of the collapsible filter system 920 with the wheel balloon 951. This second configuration 922 of the collapsible filter system 920 is expandable and collapsible according to inflation and deflation of the wheel balloon 951, such as described in the preceding examples. In this example, the arms 951A-951D extend away from the guidewire 918, toward the torus 952, in directions that extend from the guidewire 918 and are angled relative to the longitudinal axis of the guidewire 918. That is, in the cross section view provided in FIG. 9C, the arms 951A-951D extend proximally, from a distal coupling 901 with the guidewire 918, to the torus 952. In this example, one or more tethering members (e.g., balloon arms, non-inflatable cords, and the like) are optionally provided to couple the torus 952 to the guidewire 918. Such additional tethering members extend radially and normally from the guidewire 918 toward the torus 952.

In the example of FIG. 9C, the second configuration 922 of the collapsible filter system 920 includes a collapsible filter 944 that is coupled to the arms of the wheel balloon 951 and, optionally, to a portion of the guidewire 918 distal to the wheel balloon 951 (not shown in FIG. 9C). In this example, the arms 951A-951D provide structural support for the collapsible filter 944 that tapers from the torus 952 toward the guidewire 918. That is, the second configuration 922 provides several substantially triangular flow cells between the distal edge of the torus and the respective edges of adjacent arms. For instance, a first substantially triangular flow cell 945 is angled relative to the longitudinal axis of the guidewire 918 and bounded by the torus portion of the balloon 951, and the first and fourth arms 951A and 951D. In the example of FIGS. 9A and 9C where four arms 951A-951D are provided, four discrete flow cells are provided. In some examples, the collapsible filter 944 floats over all or a portion of the arms 951A-952D, and terminates at the distal coupling 901, forming a common, net-like portion of the collapsible filter 944.

Although the examples of FIGS. 9B and 9C are shown with generally concave filter portions relative to a proximal end of the respective collapsible filter systems, in other examples the filters are horizontally rotated 180 degrees relative to the guidewire to provide collapsible filter systems that are convex relative to the proximal end. In some examples, concave and convex filter portions are provided together (see, e.g., FIGS. 10C and 10D).

Figure 10C:
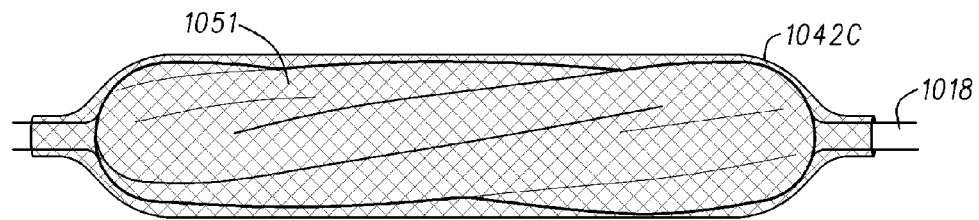
FIG. 10C illustrates generally a side view of an extended spiral balloon with convex and concave filters.

Turning now to FIGS. 10A-10D, several examples of collapsible filter systems are provided. FIG. 10A illustrates a side view of an extended spiral balloon 1051 with a collapsible filter 1042A on a guidewire 1018. The collapsible filter 1042A has a proximal filter end that is coupled to one or more of a proximal end of the balloon 1051 and the guidewire 1018 proximal to the balloon 1051. When expanded, as shown in FIG. 10A, the collapsible filter 1042A is convex relative to a proximal end of the balloon 1051. That is, the collapsible filter 1042A expands from a narrowest point at its proximal filter end to a filter opening 1043A, or filter mouth. The porosity of the collapsible filter 1042A is uniform or variable. In a first example, a proximal portion of the collapsible filter 1042A (near a coupling with the guide wire 1018) has a greater void fraction than a distal portion of the filter. That is, the filter has more pores per unit area, or has pores with a greater cross-sectional area per unit area, in the proximal portion relative to the distal portion. In another example, the ratio of the void fractions of the proximal and distal portions are reversed (with the greater void fraction at the distal portion). Optionally, other distributions of porosity are provided (e.g., a filter having greater porosity in a central portion relative to proximal and distal portions).

FIG. 10B illustrates generally a side view of the extended spiral balloon 1051 with a collapsible filter 1042B on the guidewire 1018. The collapsible filter 1042B is a mirrored version of the collapsible filter 1042A in FIG. 10A. That is, the collapsible filter 1042B has a distal filter end that is coupled to one or more of a distal end of the balloon 1051 and the guidewire 1018 distal to the balloon 1051. When expanded, as shown in FIG. 10B, the collapsible filter 1042B is concave relative to a proximal end of the balloon 1051. That is, the collapsible filter 1042B tapers from a filter opening 1043B at its proximal filter end to a narrowest point at the distal filter end. The porosity of the collapsible filter 1042B can be uniform or variable, such as described above in the example of FIG. 10A.

FIG. 10C illustrates generally a side view of the extended spiral balloon 1051 with a collapsible filter 1042C on the guidewire 1018. The collapsible filter 1042C is a combined version of the collapsible filters 1042A of FIGS. 10A and 1042B of FIG. 10B. That is, the collapsible filter 1042C has a proximal filter end that is coupled to one or more of a proximal end of the balloon 1051 and the guidewire 1018 proximal to the balloon 1051, and the collapsible filter 1042C has a distal filter end that is coupled to one or more of a distal end of the balloon 1051 and the guidewire 1018 distal to the balloon 1051. When expanded, as shown in FIG. 10C, the collapsible filter 1042C substantially encapsulates the balloon 1051 with convex and concave portions relative to a proximal end of the balloon 1051.

Figure 10D:
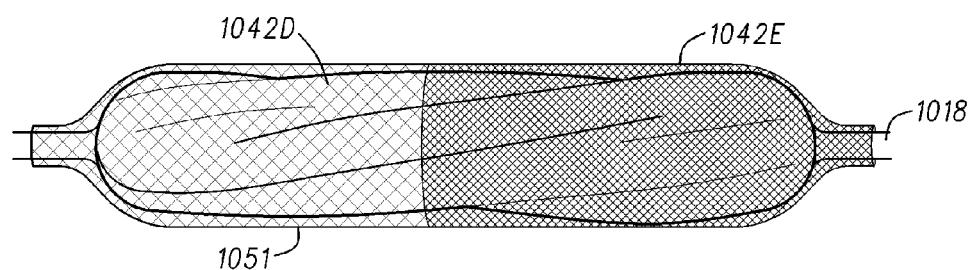
FIG. 10D illustrates generally a side view of an extended spiral balloon with convex and concave filters having different void fractions.

FIG. 10D illustrates generally a side view of the extended spiral balloon 1051 including a convex portion 1042D and a concave portion 1042E. The convex portion 1042D includes a filter having a first void fraction, and the concave portion 1042E includes a filter having a second void fraction, such that particulate matter may pass through the convex portion 1042 and is entrapped by the concave portion 1043. The void fraction of the convex and concave portions 1042D and 1042E is uniform or variable as described above in the preceding examples.

Figure 11:
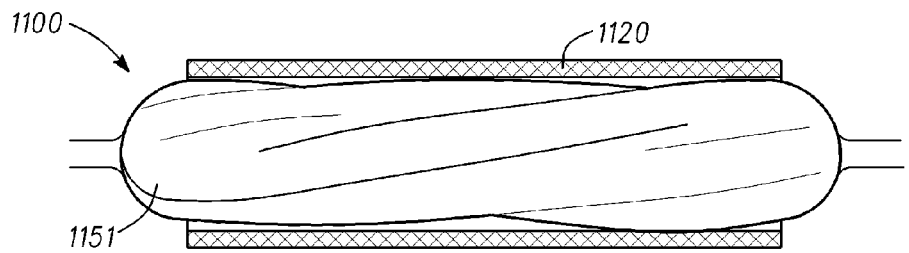
FIG. 11 illustrates generally a partial cross sectional view of a catheter including a spiral balloon inside a stent.
Figure 12:
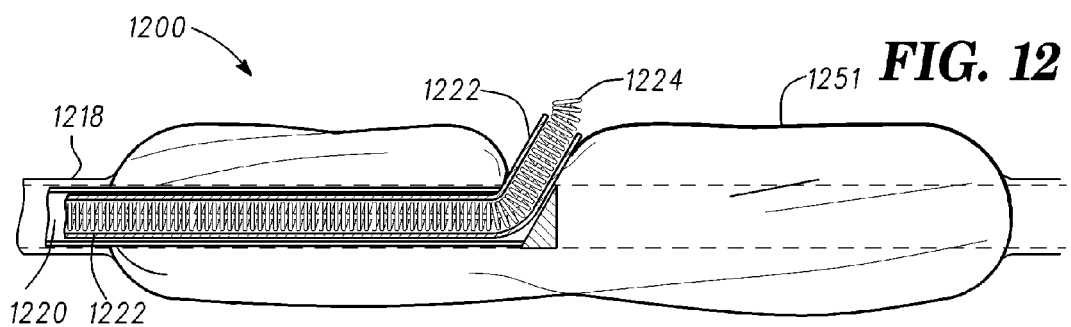
FIG. 12 illustrates generally a cross sectional view of a spiral balloon with an embolic coil.

Turning now to FIGS. 11 and 12, other applications of a non-occlusive balloon are described. For example, FIG. 11 illustrates generally an example 1100 that includes a longitudinal side view of a spiral balloon 1151 configured to deploy a stent 1120. The balloon 1151 is operable as discussed herein (e.g., similarly to the balloon 151). The balloon 1151 is inflatable and deflatable and provided with the stent 1120 extending around the balloon 1151. In a collapsed configuration, the balloon 1151 is uninflated, and the stent 1120 is collapsed around the uninflated balloon 1151 (for instance to facilitate delivery). The balloon 1151 is then inflated to an expanded configuration and the stent 1120 is correspondingly expanded and deployed. The stent 1120 optionally includes a permanent stent (or a temporary stent) that is configured for chronic positioning in a subject vessel.

After the stent 1120 is deployed, the balloon 1151 is deflated and withdrawn from the vessel.

As with the previous balloon examples, the balloon 1151 does not fully occlude fluid flow when deployed in a subject vessel. Accordingly, when the balloon 1151 is used to position a stent, fluid flow through the vessel is maintained while the stent placement procedure is underway. For example, in procedures using injected dyes or contrast to monitor fluid flow through a subject vessel flow is permitted by the balloon 1151 when inflated. In addition, the balloon 1151 provides an outward, radial force that is substantially uniform to aid in placement of the stent 1120. Accordingly, the stent 1120 is maximally apposed with the vascular wall along its length when the stent is deployed using the balloon 1151.

FIG. 12 illustrates an example 1200 that includes a cross sectional view of a spiral balloon 1251 configured to deploy an embolic coil 1224, such as to treat an aneurysm. In an example, the balloon 1251 is operable according to the discussion above, such as the discussion of the balloon 151 of FIG. 1. The balloon 1251 is provided on a guidewire 1218, and is similarly controllably inflatable and deflatable as the balloon 151. Instead of, or in addition to, the collapsible filter 142, the balloon 1251 is provided with a coil deployment sheath 1222 retaining the embolic coil 1224. The balloon 1251 is used to anchor and direct deployment of the embolic coil 1224 into an aneurysm. In an example, the coil deployment sheath 1222 is provided for one or more of anchoring or guiding the embolic coil 1224 into the aneurysm. Optionally, the embolic coil 1224 is provided near a proximal portion of the balloon 1251, and the collapsible filter 142 (previously shown in another example) extends around a distal portion of the balloon 1251 (e.g., distal to the embolic coil 1224 deployment area).

In a collapsed configuration, the balloon 1251 is collapsed and deflated, and the embolic coil 1224 is retracted substantially within a coil lumen 1220, such as in the same guidewire 1218 as is used for the balloon 1251. In an example, an inflation lumen is used with the balloon 1251, and the coil lumen 1220 is used to retain the embolic coil 1224 and guide movement of the coil into the coil deployment sheath. Optionally, in another example, the embolic coil 1224 is deployed using a separate coil sheath (not shown in the example of FIG. 12) that lies alongside the balloon 1251.

In the example of FIG. 12, the balloon 1251 is shown in the inflated, expanded configuration. Once the balloon 1251 is positioned and inflated, the embolic coil 1224 is deployable, such as by first expanding the coil deployment sheath 1222 extending through the balloon 1251 and in communication with the coil lumen 1220, and then translating the embolic coil 1224 through the coil deployment sheath 1222. In the inflated configuration, the balloon 1251 anchors the coil deployment sheath 1222 (and the embolic coil 1224) in a vessel, providing added stability while the embolic coil 1224 is placed. As previously discussed herein, the balloon 1251 includes one or more flow cells that cooperate with the delivery of the embolic coil 1224 to permit blood or other fluid flow through the vessel during the procedure. By providing improved stability for the coil sheath 1222, the embolic coil 1224 is more accurately guided toward and delivered within an aneurysm.

Expanding the coil sheath 1222 optionally includes using an internal guidewire assembly to advance one or both of the coil deployment sheath 1222 and the embolic coil 1224 out of the guidewire 1218 and toward an aneurysm. In the example of FIG. 12, the coil deployment sheath 1222 emerges from the guidewire 1218 at a central portion of the balloon 1251. That is, a portion of the coil deployment sheath 1222 is surrounded by inflated portions of the balloon 1251 and is open to the vasculature such that the coil deployment sheath 1222 and embolic coil 1224 are deployable therefrom. After the embolic coil 1224 is deployed (e.g., into an aneurysm), the coil deployment sheath 1222 is optionally withdrawn (e.g., into the coil lumen 1220), and the balloon 1251 is deflated and withdrawn from the vessel.

As described above in the discussion of FIG. 11, the balloon 1251 permits fluid flow when it is deployed in a subject vessel. Accordingly, when the balloon 1251 is used to position the embolic coil 1224, fluid flow through the vessel is maintained while the procedure is underway. For example, in procedures using injected dyes or contrast to monitor fluid flow through a subject vessel, such flow is not occluded by the balloon 1251 when it is inflated.

Figure 13:
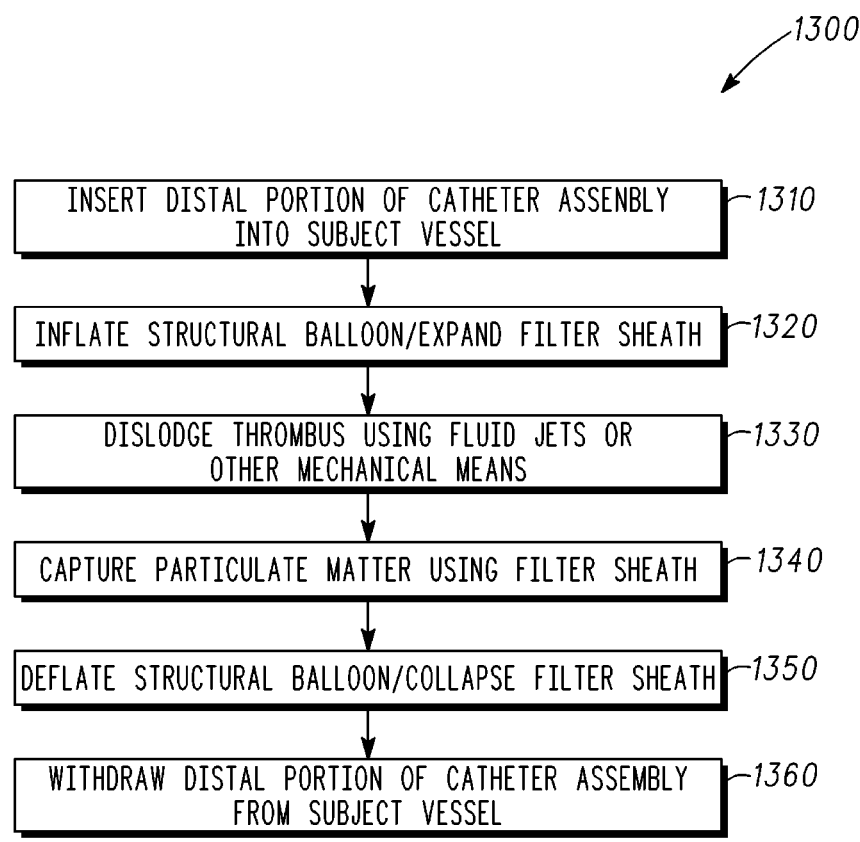
FIG. 13 illustrates a block diagram showing an example of a method of using a catheter system with a non-occlusive inflatable balloon and collapsible filter.

FIG. 13 illustrates a block diagram showing an example of a method 1300 that includes using a catheter system with a non-occlusive inflatable balloon and collapsible filter. At 1310, the method 1300 includes inserting a distal portion of a catheter assembly into a subject vessel. For example, this includes inserting the collapsible filter system 120 into a subject vessel, such as using the delivery/recovery sheath 114. At 1310, the inflatable balloon (e.g., the balloon 151) and the collapsible filter (e.g., the collapsible filter 142) is in an uninflated, collapsed configuration suitable for threading the distal portion of the catheter assembly through the subject vasculature to a treatment location.

At 1320, the structural balloon is inflated and the collapsible filter is expanded. In an example, as described above, at least a portion of the collapsible filter is coupled to, or floats on top of, the structural balloon, such that inflation of balloon portions away from a guidewire of the catheter assembly correspondingly expands the filter away from the guidewire. Inflation and expansion continue, such as until a predetermined inflation pressure is reached, until a clinician or other operator turns off the inflation source (e.g., gas or liquid), or until it is determined (e.g., automatically using a sensor or other feedback mechanism) that the filter is sufficiently apposed with the subject vessel wall. In an example, a portion of the structural balloon includes a spiral (see, e.g., FIGS. 1-5) or a torus (see, e.g., FIGS. 9A-9C) that is continuously engaged with an internal vessel surface. The filter profile is determined at least in part by the geometry of the various portions of the structural balloon.

When the structural balloon is inflated, one or more flow cells are provided, such as around or between inflated portions of the structural balloon. For example, where the structural balloon has a spiral or helical shape, a flow cell extends along a longitudinal axis of the spiral or helix and follow the curved path of the spiral or helix, such as from a proximal end of the balloon to a distal end. In some examples, the inflated structural balloon forms areas that are encircled by portions of the balloon (see, e.g., FIGS. 9A-9C) to provide flow cells therebetween.

At 1330, thrombus or other particulate matter is dislodged. For example, a fluid jet emanator, such as coupled to the same or different catheter system as the collapsible filter system 120, is provided to actively dislodge thrombus. The fluid jet emanator optionally provides multiple fluid jets that are configured to impinge upon and break up thrombus. The dislodged particulate matter then enters and travels through the vasculature, such as carried by blood or other fluids.

In an example, the fluid jet emanator is positioned proximal to the collapsible filter system 120 such that dislodged particulate matter encounters the expanded filter downstream from the emanator (see, e.g., FIG. 1). At 1340, the particulate matter is captured by the collapsible filter system 120, such as described above in FIGS. 1-10D. For instance, particulate matter passes through one or more flow cells and is captured by a filter when the filter is in the expanded configuration. In some examples, particulate matter collects near a distal end of the filter and near the guidewire because the filter tapers toward the guidewire.

At 1350, the structural balloon is deflated. Among other deflation techniques, a fluid (e.g., gas or liquid) supply line coupled to the balloon is physically severable to release the balloon inflation pressure, or a vacuum is applied to the fluid supply tube to rapidly withdraw pressurizing fluid from the balloon. In some examples, the filter is fixedly coupled to at least a portion of the structural balloon. Accordingly, the filter collapses as the balloon deflates. In some examples, a negative pressure provided by a vacuum on the balloon air supply line exerts an inward radial force on some portion of the filter such that particulate matter entrapped by the filter is clamped between the filter sheath and one or more of the structural balloon or the guidewire. This technique can compress the particulate matter to facilitate withdrawal of the catheter. In an example, after minimizing the cross-sectional profile of the distal portion of the catheter comprising the collapsible filter system, the collapsible filter system may be re-inserted into a delivery/recovery sheath, such as to further compress the particulate matter and withdraw the catheter from subject vasculature.

Additional Notes and Examples

Example 1 can include or use subject matter such as an apparatus, a method, or a means for performing acts, such as can include or use a catheter tube having a proximal portion and a distal portion, an inflatable structural balloon, coupled to the catheter tube near the distal portion, and a filter sheath coupled to the structural balloon, the filter sheath having a collapsed configuration and an expanded configuration. In Example 1, in the collapsed configuration, the filter sheath is collapsed around the catheter tube, and in the expanded configuration, the filter sheath is expanded according to inflation of the structural balloon. In Example 1, the structural balloon includes one or more inflated portions, wherein one or more flow cells extend along the one or more inflated portions and are configured to provide continuous fluid communication between proximal and distal ends of the structural balloon.

Example 2 can include, or can optionally be combined with the subject matter of Example 1, to optionally include the one or more inflated portions, including a plurality of inflated portions having one or more engagement locations coupled with the filter sheath, the one or more engagement locations at an outer edge of the structural balloon. In Example 2, in the expanded configuration, the one or more engagement locations bias the filter sheath toward a shape corresponding to the outer edge of the structural balloon.

Example 3 can include, or can optionally be combined with the subject matter of one or any combination of Examples 1 or 2 to optionally include, in the collapsed configuration, a portion of the filter sheath is collapsed around a portion of the structural balloon.

Example 4 can include, or can optionally be combined with the subject matter of one or any combination of Examples 1 through 3 to optionally include particulate matter, within the filter sheath or the flow cells in the expanded configuration, is captured between the filter sheath and the catheter tube in the collapsed configuration.

Example 5 can include, or can optionally be combined with the subject matter of one or any combination of Examples 1 through 4 to optionally include one or more flow cells, including non-occluded fluid passages extending substantially parallel to a longitudinal axis of the catheter tube.

Example 6 can include, or can optionally be combined with the subject matter of one or any combination of Examples 1 through 5 to optionally include at least one of the one or more flow cells extends from a proximal portion of the structural balloon to a distal portion of the structural balloon.

Example 7 can include, or can optionally be combined with the subject matter of one or any combination of Examples 1 through 6 to optionally include, in the expanded configuration, the one or more inflated portions of the structural balloon include ridges that extend radially from the catheter tube, the one or more flow cells between the ridges.

Example 8 can include, or can optionally be combined with the subject matter of one or any combination of Examples 1 through 7 to optionally include one or more flow cells that extend between ridges of the inflated structural balloon, and the one or more flow cells are bounded by the ridges and the filter sheath, and wherein at least a portion of one or more of the ridges includes an apex configured to impinge on a subject vessel wall.

Example 9 can include, or can optionally be combined with the subject matter of one or any combination of Examples 1 through 8 to optionally include the filter sheath is coupled to the catheter tube proximal to the structural balloon, and wherein in the expanded configuration the filter sheath is substantially convex relative to the proximal portion of the catheter tube.

Example 10 can include, or can optionally be combined with the subject matter of one or any combination of Examples 1 through 9 to optionally include the filter sheath is coupled to the catheter tube distal to the structural balloon, and wherein in the expanded configuration the filter sheath is substantially concave relative to the proximal portion of the catheter tube.

Example 11 can include, or can optionally be combined with the subject matter of one or any combination of Examples 1 through 10 to optionally include, in the expanded configuration, the structural balloon has a substantially helical shape that extends around the catheter tube along its length.

Example 12 can include, or can optionally be combined with the subject matter of one or any combination of Examples 1 through 11 to optionally include an outer edge of the structural balloon (e.g., a helical balloon) contacts one or more of a vessel wall and an inner wall of the filter sheath.

Example 13 can include, or can optionally be combined with the subject matter of one or any combination of Examples 1 through 12 to optionally include the inflatable structural balloon comprises a plurality of structural balloons, wherein each of the plurality of structural balloons are coupled to the catheter tube at different locations along the distal portion of the catheter tube, wherein the filter sheath is coupled to at least one of the plurality of structural balloons, and wherein in the expanded configuration, two or more of the plurality of structural balloons extend radially from the catheter tube in different directions.

Example 14 can include or use subject matter such as an apparatus, a method, or a means for performing acts, such as can include or use a catheter tube having a proximal portion and a distal portion, an inflatable structural balloon, coupled to the catheter tube near the distal portion, one or more longitudinal fluid passages that extend along the structural balloon and are at least partially bounded by the structural balloon, and a filter sheath deployable according to inflation of the structural balloon, the filter sheath encapsulating an end of the one or more passages such that particulate matter carried by fluid along the one or more passages is captured within the passages between the structural balloon and the filter sheath.

Example 15 can include, or can optionally be combined with the subject matter of Example 14 to optionally include, in an inflated configuration, the structural balloon includes a substantially annular vascular apposition surface configured to substantially annularly engage a subject vessel wall.

Example 16 can include, or can optionally be combined with the subject matter of one or any combination of Examples 14 or 15 to optionally include the structural balloon surrounding at least one of the longitudinal fluid passages about a longitudinal axis of the passage.

Example 17 can include, or can optionally be combined with the subject matter of one or any combination of Examples 14 through 16 to optionally include the structural balloon having one of a helical shape, a cross shape, or a toroid shape.

Example 18 can include, or can optionally be combined with the subject matter of one or any combination of Examples 1 through 17 to optionally include the filter sheath, coupled to the catheter tube both proximal and distal to the structural balloon, and wherein a proximal portion of the filter sheath has a void fraction that is greater than the void fraction of a distal portion of the filter sheath such that particulate matter passing through the proximal portion of the filter sheath is collected by the distal portion of the filter sheath.

Example 19 can include or use subject matter such as an apparatus, a method, or a means for performing acts, such as can include or use a method for deploying a filter near a distal portion of a catheter assembly in a subject vessel, the method comprising inserting a distal portion of a catheter assembly into a subject vessel, inflating at least first and second portions of a structural balloon near a distal portion of a catheter tube of the catheter assembly, the structural balloon coupled to the catheter tube, inflating including extending the at least first and second portions away from the catheter tube in different directions to form one or more flow cells therebetween, wherein the first and second portions extend between proximal and distal ends of the structural balloon, and the one or more flow cells extend between the first and second portions to provide fluid flow through the subject vessel between the proximal and distal ends of the structural balloon, expanding a filter sheath with inflating of the first and second portions of the structural balloon, the filter sheath coupled to an outer edge of the first and second portions of the structural balloon and coupled to one or more of the catheter tube or to a portion of the structural balloon near the catheter tube, the expanding including the filter sheath assuming a shape based on a balloon perimeter formed by the outer edge of the first and second portions of the structural balloon, and capturing particulate matter received by at least one of the one or more flow cells through vascular fluid flow using the filter sheath.

Example 20 can include, or can optionally be combined with the subject matter of Example 19 to optionally include expanding an outer perimeter of the filter sheath by inflating the structural balloon until the outer perimeter is substantially annularly engaged with an inner wall of the subject vessel.

Example 21 can include, or can optionally be combined with the subject matter of one or any combination of Examples 19 or 20 to optionally deflating the structural balloon, collapsing the filter sheath according to deflation of the structural balloon, including clamping the filter sheath against the deflated structural balloon, and entrapping the captured particulate matter with collapse of the filter sheath. In Example 21, capturing particulate matter includes one or both of withdrawing the catheter assembly proximally into a recovery sheath that substantially surrounds the collapsed filter sheath, or applying a negative pressure to the structural balloon.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A catheter system with an inflatable balloon and a collapsible filter, the catheter system comprising:
    a catheter tube having a proximal portion and a distal portion;
    an inflatable structural balloon, coupled to the catheter tube near the distal portion, wherein the structural balloon includes a plurality of inflatable arms, wherein each of the plurality of arms includes at least a first planar surface, wherein the first planar surface of a first inflatable arm is perpendicular to the first planar surface of a second inflatable arm; and
    a filter sheath including a proximal end and a distal end, wherein at least a portion of the distal end of the filter sheath is directly attached to the structural balloon, the filter sheath having a collapsed configuration and an expanded configuration, wherein:
        in the collapsed configuration, the filter sheath is collapsed around the cathetertube, and
        in the expanded configuration, the filter sheath is expanded according to inflation of the structural balloon, wherein one or more flow cells extend along plurality of inflatable arms and are configured to provide continuous fluid communication between proximal and distal ends of the structural balloon.

2. The catheter system of claim 1, wherein the one or more inflatable arms includes a plurality of engagement locations coupled with the filter sheath, the one or more engagement locations at an outer edge of the structural balloon, and in the expanded configuration the one or more engagement locations biases the filter sheath toward a shape corresponding to the outer edge of the structural balloon.

3. The catheter system of claim 1, wherein in the collapsed configuration, a portion of the filter sheath is collapsed around a portion of the structural balloon.

4. The catheter system of claim 3, wherein particulate matter within the filter sheath or the flow cells in the expanded configuration is configured to be captured between the filter sheath and the catheter tube in the collapsed configuration.

5. The catheter system of claim 1, wherein the one or more flow cells are non-occluded fluid passages extending substantially parallel to a longitudinal axis of the catheter tube.

6. The catheter system of claim 1, wherein at least one of the one or more flow cells extends from a proximal portion of the structural balloon to a distal portion of the structural balloon.

7. The catheter system of claim 1, wherein in the expanded configuration, the one or more inflatable arms of the structural balloon include ridges that extend radially from the catheter tube, the one or more flow cells between the ridges.

8. The catheter system of claim 7, wherein the one or more flow cells are bounded by the ridges and the filter sheath, and wherein at least a portion of one or more of the ridges includes an apex configured to impinge on a subject vessel wall.

9. A catheter system with a collapsible distal filter, the catheter system comprising:
    a catheter tube having a proximal portion and a distal portion;
    an inflatable structural balloon, coupled to the catheter tube near the distal portion, wherein the structural balloon includes a plurality of inflatable arms, wherein each of the plurality of arms includes at least a first planar surface, wherein the first planar surface of a first inflatable arm is perpendicular to the first planar surface of a second inflatable arm;
    one or more longitudinal fluid passages that extend along the structural balloon and are at least partially bounded by the structural balloon; and
    a filter sheath including a proximal end and a distal end, wherein at least a portion of the distal end of the filter sheath is directly attached to the structural balloon, wherein the filter sheath is deployable according to inflation of the structural balloon, the filter sheath encapsulating an end of the one or more passages such that particulate matter carried by fluid along the one or more passages is configured to be captured within the passages between the structural balloon and the filter sheath.

10. The catheter system of claim 9, wherein the structural balloon surrounds at least one of the longitudinal fluid passages about a longitudinal axis of the passage.

11. The catheter system of claim 9, wherein the structural balloon has a cross shape.

12. The catheter system of claim 9, wherein the filter sheath is coupled to the catheter tube both proximal and distal to the structural balloon, and wherein a proximal portion of the filter sheath has a void fraction that is greater than the void fraction of a distal portion of the filter sheath such that particulate matter passing through the proximal portion of the filter sheath is collected by the distal portion of the filter sheath.

* * * * *